United States Patent [19]

Okamoto et al.

[11] 4,139,529

[45] * Feb. 13, 1979

[54] N²-NAPHTHALENESULFONYL-L-ARGININE DERIVATIVES AND THE PHARMACEUTICALLY ACCEPTABLE ACID ADDITION SALTS THEREOF

[75] Inventors: Shosuke Okamoto; Akiko Hijikata, both of Kobe; Hyogi Kikumoto, Tokyo; Yoshikuni Tamao, Yokohama; Kazdo Ohkubo, Tokyo; Tohru Tezuka, Yokohama; Shinji Tonomura, Tokyo, all of Japan

[73] Assignees: Mitsubishi Chemical Industries Limited, Tokyo; Shosuke Okamoto, Hyogo, both of Japan

[*] Notice: The portion of the term of this patent subsequent to Jan. 3, 1995, has been disclaimed.

[21] Appl. No.: 829,483

[22] Filed: Aug. 31, 1977

Related U.S. Application Data

[60] Division of Ser. No. 760,586, Jan. 19, 1977, Pat. No. 4,066,759, which is a continuation-in-part of Ser. No. 671,436, Mar. 29, 1976, Pat. No. 4,066,758, which is a continuation-in-part of Ser. No. 622,390, Oct. 14, 1975, abandoned.

[30] Foreign Application Priority Data

| Nov. 8, 1974 | [JP] | Japan | 49-128774 |
| Nov. 8, 1974 | [JP] | Japan | 49-128775 |
| Nov. 29, 1974 | [JP] | Japan | 49-136695 |
| Nov. 29, 1974 | [JP] | Japan | 49-136697 |
| Feb. 25, 1975 | [JP] | Japan | 50-023268 |
| Feb. 26, 1975 | [JP] | Japan | 50-023635 |
| Mar. 5, 1975 | [JP] | Japan | 50-026768 |
| Mar. 11, 1975 | [JP] | Japan | 50-029857 |
| Mar. 11, 1975 | [JP] | Japan | 50-029358 |

[51] Int. Cl.² .................................................. C07D 243/00
[52] U.S. Cl. ...................... 260/239 BC; 260/239 A; 260/306.7 R; 260/307 FA; 260/308 R; 260/308 A; 260/327 R; 260/333; 260/338; 544/2; 544/3; 544/5; 544/7; 544/8; 544/54; 544/58; 544/63; 544/65; 544/66; 544/67; 544/88; 544/159; 544/179; 544/182; 544/215; 544/224; 544/335; 544/391; 548/300; 548/356
[58] Field of Search ..... 260/239 A, 239 BC, 306.7 R, 260/307 FA, 308 R, 308 A, 327 R, 333, 338; 544/2, 3, 5, 7, 8, 54, 58, 63, 65, 66, 67, 88, 159, 179, 182, 215, 224, 335, 391; 548/300, 356

[56] References Cited

U.S. PATENT DOCUMENTS

| 3,622,615 | 11/1971 | Nicolaides et al. | 560/10 |
| 3,978,045 | 8/1976 | Okamoto et al. | 260/239 B |

*Primary Examiner*—Richard Raymond
*Attorney, Agent, or Firm*—Oblon, Fisher, Spivak, McClelland & Maier

[57] ABSTRACT

N²-naphthalenesulfonyl-L-arginine esters and amides and the pharmaceutically acceptable acid addition salts thereof which have antithrombotic properties.

2 Claims, No Drawings

4,139,529

$N^2$-NAPHTHALENESULFONYL-L-ARGININE DERIVATIVES AND THE PHARMACEUTICALLY ACCEPTABLE ACID ADDITION SALTS THEREOF

RELATIONSHIP TO RELATED APPLICATIONS

This is a division of application Ser. No. 760,586 now U.S. Pat. No. 4,066,759 filed on Jan. 19, 1977 which application is a continuation-in-part of application Ser. No. 671,436 filed Mar. 29, 1976, now U.S. Pat. No. 4,066,758 which, in turn, is a continuation-in-part of U.S. application Ser. No. 622,390 filed Oct. 14, 1975, now abandoned.

BACKGROUND OF THE INVENTION:

1. Field of the Invention

This invention relates to certain new and useful $N_2$-naphthalenesulfonyl-L-arginine esters and amides, and the pharmaceutically acceptable acid addition salts thereof, which are of especial value in view of their outstanding antithrombotic properties.

2. Description of the Prior Art

In the past, there have been many attempts to obtain new and improved agents for the treatment of thrombosis. Of these, $N^2$-(p-tolylsulfonyl)-L-arginine esters are known to be effective in dissolving blood clots. (U.S. Pat. No. 3,622,615, patented Nov. 23, 1971). Also, $N^2$-dansyl-L-arginine esters and amides are disclosed in U.S. patent application Ser. No. 496,939 now U.S. Pat. No. 3,978,045. A need continues to exist, however, for a highly specific inhibitor on thrombin for the control of thrombosis.

SUMMARY OF THE INVENTION

Accordingly, one object of the present invention is to provide a class of $N^2$-naphthalenesulfonyl-L-arginine esters, amides and pharmaceutically acceptable acid addition salts thereof.

Another object of the present invention is to provide a class of $N^2$-naphthalenesulfonyl-L-arginine esters, amides and pharmaceutically acceptable acid addition salts thereof which are useful in the diagnostic selective determination of thrombin in blood and in drug therapy as antithrombotic agents in mammals.

Briefly, these objects and other objects of the present invention as hereinafter will become more readily apparent can be attained by $N^2$-naphthalenesulfonyl-L-arginine esters and amides of formula (1):

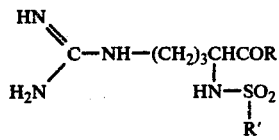
(1)

or the acid addition salts thereof with a pharmaceutically acceptable acid, wherein R is selected from the class consisting of (1) alkoxy, alkenyloxy, halogenated alkoxy and cycloalkoxy, respectively containing not more than 10 carbon atoms, aralkyloxy of not more than 15 carbon atoms, and alkoxy of not more than 10 carbon atoms substituted with an alkoxy group of not more than 10 carbon atoms;

wherein $R_1$ and $R_2$ are members selected from the class consisting of hydrogen, alkyl, aryl, alkenyl and cycloalkyl, respectively containing not more than 10 carbon atoms, and aralkyl and cycloalkylalkyl, respectively containing not more than 15 carbon atoms, and substituted alkyl containing not more than 20 carbon atoms, said substituent being selected from the class consisting of alkoxy, alkoxycarbonyl, acyl, acyloxy, arylcarbamoyl and N,N-polymethylenecarbamoyl, respectively containing not more than 10 carbon atoms, and carboxy; and

wherein Z is a divalent group containing up to 10 carbon atoms, which consists of more than one group selected from the class consisting of methylene $—CH_2—$, monosubstituted methylene

wherein $R_3$ is selected from the class consisting of alkyl, acyl, alkoxy, and alkoxycarbonyl, respectively containing not more than 10 carbon atoms, and carbamoyl, and disubstituted methylene

wherein $R_4$ and $R_5$ are alkyl groups of not more than 10 carbon atoms, and which may further contain at least one member selected from the class consisting of oxy—O—, thio —S—, cycloalkylene of not more than 10 carbon atoms, imino

alkyl-substituted imino

wherein $R_6$ is an alkyl group of not more than 10 carbon atoms, acyl-substituted imino

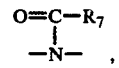

wherein $R_7$ is an alkyl group of not more than 10 carbon atoms, and phenylene

which may be arranged in any order and complete the

ring together with the said methylene, monosubstituted methylene or disubstituted methylene; and R' is a member selected from the class consisting of 1-naphthyl substituted with alkoxy or alkoxycarbonyloxy, respectively containing not more than 10 carbon atoms and 2-naphthyl substituted with alkoxy or alkoxycarbonyloxy, respectively containing not more than 10 carbon atoms.

DETAILED DESCRIPTION OF THE PREFERRED EMBODIMENTS

Now the invention is explained in detail with respect to specific aspects thereof.

In the above formula (1), examples of R are as follows:

(1) In the case of ester derivatives, examples of R are an alkoxy group containing not more than 10 carbon atoms, e.g., methoxy, ethoxy, isopropoxy, propoxy, butoxy, tertbutoxy, pentyloxy, hexyloxy and the like; a cycloalkoxy group containing not more than 10 carbon atoms, e.g., cyclohexyloxy and the like; a halogenated alkoxy group containing not more than 10 carbon atoms, e.g., 2-chloroethoxy, 4-chlorobutoxy and the like; an alkoxy group of not more than 10 carbon atoms substituted with an alkoxy group of not more than 10 carbon atoms, e.g., 2-methoxyethoxy, 2-ethoxyethoxy and the like; an alkenyloxy group containing not more than 10 carbon atoms, e.g., allyloxy, 2-butenyloxy and the like; or an aralkyloxy group containing not more than 15 carbon atoms, e.g., benzyloxy, phenethyloxy, 1-phenylethoxy, 1-phenylpropoxy and the like.

(2) In the case where

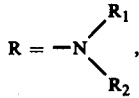

examples of $R_1$ and $R_2$ are independently a hydrogen atom, an alkyl group containing not more than 10 carbon atoms, e.g., methyl, ethyl, propyl, isopropyl, butyl, isobutyl, pentyl, hexyl, heptyl and the like; an aryl group containing not more than 10 carbon atoms, e.g., phenyl, tolyl and the like; an aralkyl group containing not more than 15 carbon atoms, e.g., benzyl, phenethyl, 3-phenylpropyl and the like; a cycloalkyl group containing not more than 10 carbon atoms, e.g., cyclopropyl, cyclohexyl and the like; a cycloalkylalkyl group containing not more than 15 carbon atoms, e.g., cyclohexylmethyl, 3-cyclohexylpropyl and the like; an alkenyl group containing not more than 10 carbon atoms, e.g., allyl, crotyl, 2-hexenyl and the like; and an alkyl group containing not more than 10 carbon atoms substituted with an alkoxy group, an alkoxycarbonyl group, an acyl group, an acyloxy group, an arylcarbamoyl group or an N,N-polymethylenecarbamoyl group, respectively containing not more than 10 carbon atoms or a carboxy group, e.g., methoxyethyl, methoxypropyl, ethoxyethyl, ethoxycarbonylmethyl, 2-ethoxycarbonylethyl, 2-methoxycarbonylethyl, 3-ethoxycarbonylpropyl, 2-acetylethyl, 2-acetoxyethyl, 2-phenylcarbamoylethyl, N,N-tetramethylenecarbamoylmethyl and the like.

(3) in the case where

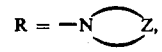

examples of R are a 1-polymethyleniminyl group, and those containing oxo or thio group, respectively containing not more than 10 carbon atoms, and a 1-polymethyleniminyl group containing not more than 10 carbon atoms substituted with an alkyl, acyl, alkoxy, or alkoxycarbonyl group, respectively containing not more than 10 carbon atoms, or carbamoyl, e.g., azetidinyl, 3-methoxy-1-azetidinyl, 3-ethoxy-1-azetidinyl, 1-pyrrolidinyl, 2-ethoxycarbonyl-1-pyrrolidinyl, 2-pyrrolidon-1-yl, piperidino, 4-piperidon-1-yl, 4-methylpiperidino, 4-ethylpiperidino, 4-propylpiperidino, 4-isopropylpiperidino, 2-methylpiperidino, 3-methylpiperidino, 2-ethoxycarbonyl-1-pyrrolidinyl, 4-methoxypiperidino, 4-oxopiperidino, 4-acetylpiperidino, 4-methoxycarbonylpiperidino, 4-carbamoylpiperidino, 1-hexamethyleniminyl, 1-octamethyleniminyl and the like; an oxazole and thiazole, such as 3-oxazolidinyl, 3-thiazolidinyl, and the like; an isoxazole and isothiazole, such as 2-isoxazolidinyl, 2-isothiazolidinyl, and the like; an oxazine, such as morpholino, 2,6-dimethylmorpholino, and an oxazine group represented by tetrahydro-1,n-oxazin-n-yl, such as tetrahydro-1,3-oxazin-4-yl and the like; a thiazine, such as tetrahydro-1,4-thiazin-4-yl and the like; 4-methyl-1-piperazinyl, 4-acetyl-1-piperazinyl, 1-piperazinyl, 2-isoindolinyl, 1-indolinyl, 1,2,3,4-tetrahydro-2-isoquinolyl, 4-azabicyclo-[3.2.2]-non-4-yl, 1,2,3,4-tetrahydro-1-quinolyl and the like.

Examples of R' are 1- or 2-naphthyl substituted with alkoxy of not more than 10 carbon atoms, e.g., methoxy, ethoxy, propoxy, isopropoxy, butoxy, isobutoxy and the like; or alkoxycarbonyloxy of not more than 10 carbon atoms, e.g., methoxycarbonyloxy, ethoxycarbonyloxy and the like.

In the formula (1), R is preferably alkoxy of 1–8 carbon atoms, aralkyloxy of 7–9 carbon atoms, alkenyloxy of 3–6 carbon atoms, cyclohexyloxy, ω-alkoxyalkoxy of 2–6 carbon atoms, ω-chloroalkoxy of 2–6 carbon atoms, alkylamino of 1–9 carbon atoms, ω-alkoxyalkylamino of 2–6 carbon atoms, ω-alkoxycarbonylalkylamino of 2–8 carbon atoms, alkenylamino of 3–5 carbon atoms, cycloalkylamino of 3–6 carbon atoms, cyclohexylmethylamino, arylamino of 6–10 carbon atoms, aralkylamino of 7–10 carbon atoms, dialkylamino of 2–10 carbon atoms, N-alkyl-N-(ω-alkoxycarbonylalkyl)amino of 4–8 carbon atoms, N-alkyl-N-(ω-alkoxyalkyl)amino of 3–8 carbon atoms, N-alkyl-N-aralkylamino of 8–10 carbon atoms, N-alkyl-N-(ω-acylalkyl)amino of 4–8 carbon atoms, N,N-polymethyleniminyl of 3–10 carbon atoms, N,N-polymethyleniminyl of 3–10 carbon atoms substituted with alkyl of 1–5 carbon atoms, alkoxy of 1–5 carbon atoms, alkoxycarbonyl of 2–5 carbon atoms, acyl of 2–5 carbon atoms, or carbamoyl; tetrahydro-1,n-oxazin-n-yl, tetrahydro-1,n-thiazin-n-yl, wherein n is an integer of 2, 3 or 4, tetrahydro-1,n-oxazin-n-yl, wherein n is an integer of 2, 3 or 4 and which is substituted with one or two alkyl groups of 1-5 carbon atoms; 2-isoindolinyl, 1-piperazinyl, 1-piperazinyl substituted with alkyl of 1-5 carbon atoms or acyl of 2-5 carbon atoms, 4-alkyl-1-piperazinyl of 5-8 carbon atoms, or 4-azabicyclo[3.2.2]-non-4-yl.

R' is preferably 5-methoxy-1-naphthyl, 1-methoxy-2-naphthyl, 6-methoxy-2-naphthyl, 7-methoxy-2-naphthyl, 5-ethoxy-1-naphthyl, 5-propoxy-1-naphthyl, 5-isopropoxy-1-naphthyl.

Typical compounds of this invention include:

(1) in the case of the ester derivatives:
N²-(7-methoxy-2-naphthalenesulfonyl)-L-arginine butyl ester, N²-(7-methoxy-2-naphthalenesulfonyl)-L-arginine 2-methoxyethyl ester, N²-(7-methoxy-2-naphthalenesulfonyl)-L-arginine benzyl ester, N²-(7-methoxy-2-naphthalenesulfonyl)-L-arginine 3-chloropropyl ester, N²-(7-methoxy-2-naphthalenesulfonyl)-L-arginine hexyl ester.

(2) In the case of the amide derivatives, wherein

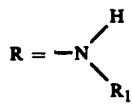 (i)

(R₁ is not hydrogen): N²-(5-methoxy-1-naphthalenesulfonyl)-N-(2-methoxyethyl)-L-argininamide, N²-(5-methoxy-1-naphthalenesulfonyl)-N-(2-methoxycarbonylethyl)-L-argininamide, N²-(7-methoxy-2-naphthalenesulfonyl)-N-(2-methoxycarbonylethyl)-L-argininamide,

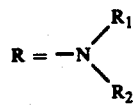 (ii)

(neither R₁ nor R₂ is hydrogen): N²-(5-methoxy-1-naphthalenesulfonyl)-N-methyl-N-butyl-L-argininamide,

 (iii)

4-ethyl-1-[N²-(5-methoxy-1-[N4-methyl-1-[N²-(5-methoxy-1-naphthalenesulfonyl)-L-arginyl]piperidine, N²-(5-methoxy-1-naphthalenesulfonyl)-N,N-hexamethyleneiminyl-L-argininamide, 4-[N²-(5-methoxy-1-naphthalenesulfonyl)-L-arginyl]morpholine, 4-ethyl-1-[N²-(6-methoxy-2-naphthalenesulfonyl)-L-arginyl]piperidine, 4-ethyl-1-[N²-(5-ethoxy-1-naphthalenesulfonyl)-L-arginyl]piperidine, 4-ethyl-1-[N²-(7-methoxy-2-naphthalenesulfonyl)-L-arginyl]-piperidine, 4-methyl-1-[N²-(7-methoxy-2-naphthalenesulfonyl)-L-arginyl]piperidine, 1-[N²-(7-methoxy-2-naphthalenesulfonyl)-L-arginyl]piperidine, 4-[N²-(7-methoxy-2-naphthalenesulfonyl)-L-arginyl]morpholine, 4-acetyl-1-[N²-(6-methoxy-2-naphthalenesulfonyl)-L-arginyl]piperidine, 4-methoxy-1-[N²-(7-methoxy-2-naphthalenesulfonyl)-L-arginyl]piperidine, 4-methoxycarbonyl-1-[N²-(6-methoxy-2-naphthalenesulfonyl)-L-arginyl]piperidine, 4-[N²-(5-methoxy-1-naphthalenesulfonyl)-L-arginyl]tetrahydro-1,4-thiazine, 4-methyl-1-[N²-(5-methoxy-1-naphthalenesulfonyl)-L-arginyl]-piperazine, 4-acetyl-1-[N²-(5-methoxy-1-naphthalenesulfonyl)-L-arginyl]piperazine.

These typical compounds are highly potent in their antithrombotic activity.

For the preparation of the compounds of this invention, various methods can be employed depending upon the particular starting materials and/or intermediates involved. Successful preparation of these compounds is possible by way of several synthetic routes which are outlined below.

(1) Preparation of N²-naphthalenesulfonyl-L-arginine esters.

(a) Esterification of an N²-naphthalenesulfonyl-L-arginine.

N²-naphthalenesulfonyl-L-arginines, which are the starting materials for the preparation of N²-naphthalenesulfonyl-L-arginine esters, are most generally obtained by reacting L-arginine and a naphthalenesulfonyl halide, in the presence of a base.

The naphthalenesulfonyl halides to be used are represented by the general formula R'—SO₂X, wherein R' is the same as in formula (I) and X is a halogen atom such as chlorine or bromine. Usually a naphthalenesulfonyl chloride is preferred.

However, N²-naphthalenesulfonyl-L-arginines may also be obtained by reacting ornithine, the ω-position of which is protected, with a naphthalenesulfonyl halide in the presence of a base, removing the protective group at the ω-position of the product, and thereafter guanidylating the N²-naphthalenesulfonylornithine by conventional procedures.

N²-naphthalenesulfonyl-L-arginine esters or acid addition salts thereof are prepared by esterifying the above-mentioned N²-naphthalenesulfonyl-L-arginine in accordance with the processes explained below.

(i) Esterification by heating an N²-naphthalenesulfonyl-L-arginine and an alcohol.

The reaction rate is low in this method, which is therefore conducted under high pressure at an elevated temperature. Care must be exercised, since N²-naphthalenesulfonyl-L-arginines are easily decomposed at high temperatures.

(ii) Esterification of an N²-naphthalenesulfonyl-L-arginine with an alcohol in the presence of an esterification catalyst.

Suitable esterification catalysts include hydrogen halides, such as hydrogen chloride, hydrogen bromide or the like; mineral acids such as sulfuric acid, nitric acid, phosphoric acid, or the like; organic acids, such as toluenesulfonic acid, benzenesulfonic acid, methanesulfonic acid, trifluoromethanesulfonic acid, trifluoroacetic acid, cationic ion exchange resins or the like; and Lewis acids, such as boron trifluoride, aluminium chloride, or the like. Strong acids are especially suitable.

A strong acid esterification catalyst adds to an N²-naphthalenesulfonyl-L-arginine ester to form an acid addition salt thereof. Normally, 1 equivalent of the acid add to 1 equivalent of the N²-naphthalenesulfonyl-L-arginine ester and therefore, 1 equivalent or more of the esterification catalyst are preferably used for each 1 equivalent of the N²-naphthalenesulfonyl-L-arginine.

Suitable alcohols for the above-mentioned esterification include primary,, secondary, and tertiary alkyl alcohols containing up to 10 carbon atoms, such as methanol, ethanol, propanol, isopropyl alcohol, butanol, tert-butyl alcohol, pentanol, hexanol, 2-ethylhexanol; aralkyl alcohols containing up to 15 carbon atoms, such as benzyl alcohol, phenethyl alcohol, 1-phenylethanol, 1-phenyl-1-propanol, or the like; alkenyl alcohols containing up to 10 carbon atoms, such as allyl alcohol, crotyl alcohol, methyl vinyl carbinol, or the like; cycloalkyl alcohols containing up to 10 carbon atoms, such as cyclohexanol, cyclopentanol, or the like; and alkyl alcohols containing up to 10 carbon atoms substituted with an alkoxy group of up to 10 carbon atoms or a halogen, such as 3-chloro-1-propanol, 2-chloro-1-propanol, 1-chloro-2-propanol, 2-fluoro-1-ethanol, 2-chloro-1-ethanol, 4-chloro-1-butanol, 2-methoxyethanol, 3-ethoxypropanol, or the like.

An $N^2$-naphthalenesulfonyl-L-arginine reacts with an equimolar amount of an alcohol. However, at least 5 moles of the alcohol per mole of the $N^2$-naphthalenesulfonyl-L-arginine are preferably employed to enhance the reaction rate.

The esterification reaction can be carrier out in a reaction-inert solvent, such as an aromatic hydrocarbon, e.g., benzene, toluene, xylene, or the like; a chlorinated hydrocarbon, e.g., carbon tetrachloride, chloroform dichloromethane, or the like; a hydrocarbon solvent, e.g., hexane, cyclohexane, or the like; an ether, e.g., dioxane, tetrahydrofuran, or the like; or a mixture of these compounds. Especially preferred solvents include benzene, toluene, xylene, cyclohexane, carbon tetrachloride and dichloromethane, which form azcotropic mixtures with water, and are therefore advantageous for the esterification reaction, since water formed during the reaction can be easily removed, and the reaction can be carried out advantageously at equilibrium.

The reaction temperature varies with the alcohol and the catalyst to be employed. Generally, the temperature ranges from 0° C. to the boiling point of the alcohol or solvent. The reaction time varies widely with the alcohol and catalyst employed and normally ranges from 10 minutes to 13 hours.

After the reaction is completed the alcohol and/or solvent is distilled off, and an $N^2$-naphthalenesulfonyl-L-arginine ester or an acid addition salt thereof is obtained. Normally, 1 equivalent of the acid esterification catalyst adds to the $N^2$-naphthalenesulfonyl-L-arginine ester. The acid addition salt can be easily converted to the corresponding $N^2$-naphthalenesulfonyl-L-arginine ester by adjusting the pH of the medium.

The $N^2$-naphthalenesulfonyl-L-arginine esters and the acid addition salts thereof can be purified by recrystallization from a combination of solvents, such as ethyl ether, alcohols, acetone or the like, or reprecipitating by addition of ether to an alcohol solution of the compounds.

(iii) Esterification of an $N^2$-naphthalenesulfonyl-L-arginine with an alcohol and a thionyl halide.

Suitably thionyl halides include thionyl chloride and thionyl bromide. The $N^2$-naphthalenesulfonyl-L-arginine reacts with an equimolar amount of the thionyl halide. However, it is desirable to employ at least 2 moles of the thionyl halide per one mole of the $N^2$-naphthalenesulfonyl-L-arginine in order to drive the reaction to completion. During the reaction, the thionyl halide decomposes to a hydrogen halide and $SO_2$, and the formed hydrogen halide adds to the $N^2$-naphthalenesulfonyl-L-arginine ester to generally form a halogeno acid salt of the $N^2$-naphthalenesulfonyl-L-arginine ester.

The other reaction conditions and the procedures for separation and purification of the product are the same as in process (ii) (esterification with an esterification catalyst).

(iv) Preparation of an $N^2$-naphthalenesulfonyl-L-arginine methyl ester.

An $N^2$-naphthalenesulfonyl-L-arginine methyl ester can be prepared by the reaction of an $N^2$-naphthalenesulfonyl-L-arginine with diazomethane; reaction of an $N^2$-naphthalenesulfonyl-L-arginine with dimethyl sulfite and tosylsulfonic acid; and reaction of an $N^2$-naphthalenesulfonyl-L-arginine with dimethyl sulfate.

(v) Reaction of an alkali metal salt of an $N^2$-naphthalenesulfonyl-L-arginine with an alkyl halide.

Alkyl esters of an $N^2$-naphthalenesulfonyl-L-arginine can be prepared by reacting an alkali metal salt of an $N^2$-naphthalenesulfonyl-L-arginine and an alkyl halide in a polar solvent.

In addition, an $N^2$-naphthalenesulfonyl-L-arginine may be esterified by other processes, but processes (ii) and (iii) are generally used.

(b) Reaction of an L-arginine ester with a naphthalenesulfonyl halide.

L-arginine esters or acid addition salts thereof, which are used as the starting material of $N^2$-naphthalenesulfonyl-L-arginine esters or acid addition salts thereof, are most generaly obtained by reacting L-arginine with an alcohol in the presence of an acid catalyst. When the esterification is carried out in the presence of an acid catalyst, an acid addition salt of an L-arginine ester is usually obtained.

The naphthalenesulfonyl halides usable for this process has been defined hereinbefore.

The reaction of an L-arginine ester or an acid addition salt thereof with a naphthalenesulfonyl halide is normally carried out in the presence of a base. The base captures the hydrogen halide formed during the reaction and enhances the reaction rate.

Suitable bases include organic bases, such as triethylamine, pyridine, or the like; and common inorganic bases such as sodium hydroxide, potassium hydroxide, potassium carbonate, or the like. The inorganic bases are usually used as an aqueous solution.

The base is normally used in an amount at least equivalent to the L-arginine ester. When an acid addition salt of an L-arginine ester is used as the starting material, an excess of the base sufficient to convert the L-arginine ester acid addition salt to the L-arginine ester is desirably used in addition to the amount to be used as the catalyst.

The naphthalenesulfonyl halide reacts with an equimolar amount of an L-arginine ester or an acid addition salt thereof. The reaction of an L-arginine ester of an acid addition salt thereof and a naphthalenesulfonyl halide is usually carried out in a solvent. Suitable solvent include water; chlorinated solvents, such as dichloromethane, chloroform, carbon tetrachloride, and the like; aromatic hydrocarbons, such as benzene, toluene xylene and the like; ethers such as ethyl ether, tetrahydrofuran, tetrahydropyran and the like; ketone such as acetone, methyl ethyl ketone, cyclohexanone and the like; basic solvents, such as dimethylacetamide, dimethylformamide, tetramethylurea, N-methylpyrrolidone, pyridine, quinoline, and the like; or a mixture of two or more of these solvents. A basic solvent acts as an acid acceptor, and therefore the addition of the base is unnecessary when such solvent is used.

The reaction temperature is dependent on the arginine esters and bases to be employed, but is generally between 0° C. and the boiling temperature of the solvent employed.

The reaction time varies with the arginine ester and is usually between 10 minutes and 15 hours.

After the reaction is completed, the produced salt is washed away with water, the solvent is removed by distillation, and the obtained product is washed with water and/or the solvent. To the thus obtained $N^2$-naphthalenesulfonyl-L-arginine ester, an acid (e.g., hydrochloric acid, p-toluenesulfonic acid, or the like) is added, and the formed acid addition salt of the $N^2$-naphthalenesulfonyl-L-arginine ester is isolated.

(2) Preparation of $N^2$-naphthalenesulfonyl-L-argininamides.

(a) Reaction of an $N^2$-naphthalenesulfonyl-L-argine ester with a primary amine.

Suitable $N^2$-naphthalenesulfonyl-L-arginine esters or the acid addition salts thereof include the methyl ester, ethyl ester, isopropyl ester and the like or the hydrochlorides thereof. Suitable amines include primary amines, such as an alkylamine containing not more than 10 carbon atoms, e.g., methylamine, ethylamine, propylamine, isopropylamine, butylamine, hexylamine, heptylamine and the like; an aralkylamine containing not more than 15 carbon atoms, e.g., phenethylamine and the like; a cycloalkylamine containing not more than 10 carbon atoms, e.g., cyclopropylamine, cyclobutylamine, cyclopentylamine, cyclohexylamine, cyclooctylamine, 4-methylcyclohexylamine, and the like; an alkylamine containing not more than 10 carbon atoms substituted with an alkoxy group containing not more than 10 carbon atoms, e.g., 2-methoxyethylamine, 2-ethoxyethylamine, 3-methoxypropylamine, 3-methoxybutylamine, 3-methoxypenylamine and the like; a cycloalkylalkylamine containing not more than 15 carbon atoms, e.g., cyclohexylmethylamine, 2-cyclohexylethylamine, cyclobutylmethylamine, 3-cyclopentylbutylamine and the like, and an alkenylamine containing not more than 10 carbon atoms, e.g., allylamine, crotylamine, 3-butenylamine and the like.

The amine is preferably used in an amount equivalent to or greater than the $N^2$-naphthalenesulfonyl-L-arginine ester. The amine is preferably used in excess in order to enhance the reaction rate and to carry out the reaction advantageously at equilibrium. The amine is usually used in an amount 2 to 10 times the molar quantity of the $N^2$-naphthalenesulfonyl-L-arginine ester. When an acid addition salt of an $N^2$-naphthalenesulfonyl-L-arginine ester is used, the amine is usually converted to an acid addition salt. Therefore, it is necessary to use an amine corresponding to the acid addition salt of the amine to be formed in excess.

A basic compound may be used as a catalyst. Specifically, an alkali metal alkoxide, such as sodium methoxide or a tertiary amine, such as pyridine or the like are preferable. When these catalysts are used, the reaction rate is enhanced and therefore the amine can be used in a lesser amount and milder reaction conditions are thus possible.

If the amine is used in large excess, $N^2$-naphthalenesulfonyl-L-arginine esters or acid addition salts thereof will dissolve in the amine, and therefore the reaction will proceed without a solvent. However, solvents, such as alcohols, e.g., methanol, ethanol. butanol and the like; ethers; e.g., ethyl ether, tetrahydrofuran, tetrahydropyran, dioxane and the like; hydrocarbons, e.g., benzene, toluene, cyclohexane and the like; halogenated hydrocarbons, e.g., carbon tetrachloride, chloroform, dichloromethane and the like; and water can be used.

The reaction is usually carried out by mixing an $N^2$-naphthalenesulfonyl-L-arginine ester or an acid addition salt thereof with an excess amount of an amine, the resulting homogeneous solution is allowed to stand at room temperature. However, the reaction mixture can be heated to a temperature up to the boiling temperature of the amine of solvent to enhance the reaction rate.

The reaction time is dependent on the basicity and amount of the amine employed, among other factors, but usually ranges from several hours to several days.

After the reaction is completed, the product is collected by filtration, washed with water, and purified by recrystallization from a suitable solvent, e.g., aqueous methanol, or the like. If solid product does not form, the excess amine and/or the solvent is removed by distillation, and the residue is washed and purified by recrystallization from a suitable solvent.

(b) Reaction of an L-argininamide with a naphthalenesulfonyl halide.

An L-argininamide or an acid addition salt thereof can be obtained by protecting the guanidine group and α-amino group of the arginine via nitration, acetylation, formylation, phthaloylation, trifluoroactylation, p-methoxybenxyloxy-carbomylation, benzoylation, benzyloxycarbonylation, t-butoxycarbonylation or tritylation, then condensing the obtained arginine derivative with an amine by a conventional method such as the acid halide method, azide method, mixed anhydride method, activated ester method, carbodiimide method, or the like, and thereafter removing the protective group by the known method. the suitable naphthalenesulfonyl halides have already been explained hereinbefore with respect to the preparation of $N^2$-naphthalenesulfonyl-L-arginines.

The reaction of an L-argininamide or an acid addition salt thereof and a naphthalenesulfonyl halide is usually carried out in the presence of a base. The basic compound captures the hydrogen halide which is formed during the reaction, and thus promotes the reaction.

Suitable bases include organic bases such as triethylamine, pyridine and the like; or inorganic bases, such as sodium hydroxide, potassium hydroxide, potassium carbonate and the like. Inorganic bases are usually used as an aqueous solution.

The base is used in excess of the amount equivalent to the L-argininamide. When an acid addition salt of an L-argininamide is used, a base is preferably used in an amount sufficient to convert the acid addition salt of the L-argininamide to the free L-argininamide in addition to the amount of the base to be used as the catalyst.

A naphthalenesulfonyl halide is usually reacted with an equimolar amount of an L-argininamide or an acid addition salt thereof in a solvent. Suitable solvents include water; chlorinated hydrocarbons such as dichloromethane, chloroform, carbon tetrachloride and the like; aromatic hydrocarbons, such as benzene, toluene, xylene and the like; others, such as ethyl ether, tetrahydrofuran, dioxane, tetrahydropyran and the like; ketones, such as acetone, methyl ethyl ketone, cyclohexanone and the like; basic solvents, such as dimethylacetamide, dimethylformamide, tetramethylurea, N-methylpyrrolidone, pyridine quinoline and the like; or a mixture of two or more of these solvents. A basic solvent acts as an acid acceptor, and therefore further addition of the base is not required in these instances.

The reaction temperature is dependent on the species of the L-argininamide and base, but usually between 0°

C. and the boiling temperature of the solvent. the reaction time varies with the L-argininamide and is usually between 10 minutes and 15 hours.

After the reaction is completed, the formed salt is removed by washing with water, solvent is removed by distillation, and the obtained product is washed with water and/or the solvent, and the $N^2$-naphthalenesulfonyl-L-argininamide is obtained. The thus obtained $N^2$-naphthalenesulfonyl-L-argininamide can be isolated in the form of an acid addition salt thereof by the addition of an acid (e.g., hydrochloric acid, p-toluenesulfonic acid, and the like).

(c) Elimination of the $N^G$-substituted from an $N^G$-substituted-$N^2$-naphthalenesulfonyl-L-argininamide having the formula (II).

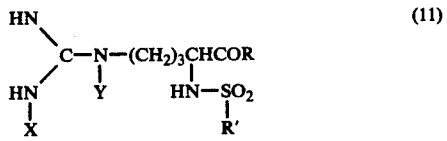

An $N^2$-naphthalenesulfonyl-L-argininamide is prepared by eliminating the $N^G$-substituent from an $N^G$-substituented-$N^2$-naphthalenesulfonyl-L-argininamide having the above formula (II) by means of acidolysis or hydrogenolysis. In the formula (II), R and R' are the same as in the formula (I), N and Y are selected from hydrogen and protective groups for the guanidino group, and at least one of them is a protective. group. Suitable protective groups include nitro tosyl, trityl, or an oxycarbonyl such as benzyloxycarbonyl, p-nitrobenzyloxycarbonyl, p-methoxybenzyloxycarbonyl, tert-butoxycarbonyl and the like.

The $N^G$-substituted-$N^2$-naphthalenesullonyl-L-argininamides as represented by general formula (II) or acid addition salts thereof can be obtained by condensing an $N^G$-substituted $N^2$-substituted arginine (usually the $N^2$-substituent is a protective group for the amino group, such as benzyloxycarbonyl, t-butoxycarbonyl, or the like) and an amine via the azide method, mixed anhydride method, activated ester method, carbodiimido method or the like, selectively removing only the $N^2$-substituent by means of catalytic hydrogenolysis or acidolysis, and reacting the thus obtained $N^G$-substituted-L-argininamide or an acid addition salt thereof with a naphthalenesulfonyl halide, as defined in the above, in the presence of a base in a solvent. Suitable based include organic bases, such as triethylamine, pyridine and the like; or inorganic bases, such as sodium hydroxide, potassium hydroxide, potassium carbonate, sodium hydrogen carbonate and the like. Inorganic bases are normally used as an aqueous solution.

The base is preferably used in an amount not less than the amount equivalent to the $N^G$-substituted-L-argininamide. When an acid addition salt of an $N^G$-substituted-L-argininamide is used, the base is preferably used in an amount sufficient to neutralize the acid addition salt in addition to the amount to be used as the catalyst. The naphthalenesulfonyl halide is normally used in an equimolar amount to the $N^G$-substituted-L-argininamide.

Suitable solvents include water; chlorinated solvents, such as dichloromethane, chloroform, carbon tetrachloride and the like; aromatic hydrocarbons, such as benzene, toluene, xylene and the like; ethers, such as ethyl ether, tetrahydrofuran, dioxane and the like; ketones, such as acetone, methyl ethyl ketone, cyclohexanone, and the like; basic solvents such as dimethylacetamide, dimethylformamide, tetramethylurea, N-methylpyrrolidone, pyridine, quinoline, and the like; or a mixture of two or more of the above-mentioned solvents. A basic solvent acts as an acid acceptor, and therefore further addition of the base is not required in these instances.

The reaction temperature is dependent on the $N^G$-substituted-L-argininamide and base, but usually ranges from $-10°$ C. to the boiling temperature of the solvent.

The reaction time varies with the species of the $N^G$-substituted-L-argininamide and base, and the reaction temperature, and is usually from 5 minutes to 24 hours.

After the reaction is completed, the solvent and base are distilled off, the formed salt is removed by washing with water, and the $N^G$-substituted-$N^2$-naphthalenesulfonyl-L-argininamide is purified by recrystallizing or reprecipitating from a suitable solent. The reaction product may also be separated and purified by means solvents, chromatography. Suitable elutants include chlorinated solvemts, such as chloroform, dichloromethane and the like; a chlorinated solvent containing alcohol and the like.

As explained above, the $N^2$-naphthalenesulfonyl-L-argininamide represented by general formula (II) or an acid addition salt thereof is obtained from the $N^G$-substituted-$N^2$-naphthalenesulfonyl-L-argininamide by removing the $N^G$-substituent, which is a protective group for the guanidino group of the amide, via hydrogenolysis or acidolysis.

Suitable acids for the acidolysis include hydrogen halides, such as hydrogen chloride, hydrogen bromide, hydrogen fluoride; and organic acids, such as trifluoroacetic acid, trifluoromethanesulfonic acid, formic acid, acetic acid, and the like.

The acidolysis is preferably carried out by treating the $N^G$-substituted-$N^2$-naphthalenesulfonyl-L-argininamide or the acid addition salt thereof with any of the above-mentioned acids without a solvent or in a solvent, such as an alcohol, e.g., methanol, ethanol and the like; an ether, e.g., tetrahydrofuran, dioxane, anisole and the like; an organic acid, e.g., acetic acid and the like; or an ester, e.g., ethyl acetate and the like, at a temperature between $-10°$ C. and $+100°$ C., preferably at room temperature. The time required for the acidolysis varies with the acid and solvent, the protective $N^G$-substituent, and the temperature of treatment, and is from 30 minutes to 24 hours.

After the decomposition is completed, the $N^2$-naphthalenesulfonyl-L-argininamide or an acid addition salt thereof is obtained by removing the solvent and the excess acid or adding to the reaction mixture an inert solvent, such as ethyl ether, petroleum ether, a hydrocarbon solvent, or the like so as to form a precipitate and collecting the precipitate. An excess of he acid is usually used, and therefore the $N^2$-naphthalenesulfonyl-L-argininamide which is obtained by removing the protective group is in the form of an acid addition salt. This salt can be easily converted to a free amide by neutralization.

Hydrogenolysis can be carried out according to any of the general procedures of reductive hydrogenation, although catalytic hydrogenation is most advantageous. Catalytic hydrogenation is carried out in the presence of a hydrogenactivating catalyst in a hydrogen atmosphere. Suitable hydrogen-activating catalyst include Raney nickel, palladium, platinum and the like. Suitable solvents include alcohols, such as methanol, ethanol and the like; ethers, such as dioxane, tetrahydrofuran and the like; organic acids, such as acetic acid, propionic acid and the like; or a mixture of two or more of the above-mentioned solvents.

The reaction temperature is dependent on the protective group for the guanidino group and the activity of the employed catalyst, and is usually between 0° C. and the boiling temperature of the solvent. The hydrogen pressure is dependent on the reaction temperature and activity of the catalyst. Atmospheric pressure is sufficient for the reaction, although higher pressure may be employed. The reaction time is dependent on the activity of the catalyst, the reaction temperature, the hydrogen pressure and the like and is usually from 2 hours to 120 hours.

After the hydrogenolysis is finished, the catalyst is removed by filtration, the solvent is removed by distillation, and the $N^2$-naphthalenesulfonyl-L-argininamide or the acid addition salt thereof is obtained. The acid addition salt is easily converted to the free $N^2$-naphthalenesulfonyl-L-argininamide by neutralization.

The thus obtained $N^2$-naphthalenesulfonyl-L-argininamide or the acid addition salt thereof is purified by recrystallization from a solvent which is a mixture of two or more of the following: water, ethyl ether, alcohols, acetone, or the like, or by reprecipitation by addition of ethyl ether to an alcohol solution of the compound.

The $N^2$-alkoxynaphthalenesulfonyl-L-arginines which are the starting materials for the preparation of $N^2$-alkoxynaphthalenesulfonyl-L-arginyl halides (IX) may include some new compounds which can be conventionally prepared by the condensation of L-arginine with a substantially equimolar amount of the alkoxynaphthalenesulfonyl halide (III) by a method similar to that described in he condensation of an L-argininamide with a naphthalenessulfonyl halide.

A number of amino acid t-butyl esters used as starting materials in the preparation of the herein claimed compounds have not previously been reported in the chemical literature. However, such compounds are easily prepared from conventional procedures such as is taught by A. J. Speziale et al J. Organic Chemistry 25 731 (1960).

Certain of the dialkoxy naphthalene sulfonyl chlorides used as starting materials herein also have not previously been reported in the chemical literature such as 6,7-dimethoxy-2-naphthalene-sulfonyl chloride. However, this compound is also preparable by known procedures, such as are described by E. H. Rodd, *Chemistry of Carbon Compounds*, Elsevier Publishing Company, 1954, Volume III, pp. 441–469.

(d) Reaction of an $N^2$-naphthalenesulfonyl-L-arginyl halide and an amine.

An $N^2$-naphthalenesulfonyl-L-argininamide is prepared by reaction of a corresponding $N^2$-naphthalenesulfonyl-L-arginyl halide and an amine. The $N^2$-naphthalenesulfonyl-L-arginyl halide is pepared by reacting a corresponding $N^2$-naphthalenesulfonyl-L-arginine with a halogenating agent such as thionyl chloride, phosphorus oxychloride, phosphorus trichloride, phosphorus pentachloride, phosphorus tribromide, etc.

Although the halogenation proceeds without solvent, an inert solvent such as chlorinated hydrocarbons, e.g., chloroform, dichloromethane, etc., ethers, e.g., tetrahydrofuran, dioxane, etc., may peferably be used.

Usually the halogenating agent is used at least in an equimolar amount to the $N^2$-naphthalenesulfonyl-L-arginine.

The amount of the solvent to be used is not critical. But it is suitable to use a solvent in an amount 5 - 100 times the weight of the $N^2$-naphthalenesulfonyl-L-arginine.

The preferred reaction temperature is in the range of from −10° C. to room temperature. The reaction time varies with the halogenating agent and reaction temperature, and usually is from 15 minutes to 5 hours.

Amidation proceeds without solvent, but the use of a solvent such as dimethylformamide, and halogenated solvent (chloroform, dichloromethane, etc.), gives better results. Usually the amine is used at least in an equimolar amount to the $N^2$-naphthalenesulfonyl-L-arginyl halide.

The amount of the solvent to be used is not critical, but is usually about 5 - 100 times by weight the amount of the $N^2$-naphthalenesulfonyl-L-arginyl halide.

The preferred reaction temperature is in the range of from −10° C. to room temperature. The reaction time depends on the species of the amine and usually is from 5 minutes to 10 hours.

(c) Guanidylation of an $N^2$-naphthalenesulfonyl-L-ornithinamide or of an acid addition salt thereof.

An $N^2$-naphthalenesulfonyl-L-argininamide or an acid addition salt thereof is prepared by guanidylating a corresponding $N^2$-naphthalenesulfonyl-L-ornithinamide or an acid addition salt thereof. The guanidylation is performed by using ordinary guanidylating agents such as an O-alkylisourea, an S-alkylisothiourea, 1-guanyl-3,5-dimethylpyrazole, carbodiimide, etc., and O-alkylisourea and S-alkylisothiourea are especially preferred guanidylating agents.

The reaction of the $N^2$-naphthalenesulfonyl-L-ornithinamide or its acid addition salt with an O-alkylisourea or an S-alkylisothiourea is carried out usually in the presence of a base. The bases to be used include oganic bases such as triethylamine, pyridine, etc.; common inorganic bases such as sodium hydroxide, potassium hydroxide, potassium carbonate, etc. Inorganic bases are usually used in the form of an aqueous solution.

The base is used in an amount of 0.01 to 0.1 equivalent to the $N^2$-naphthalenesulfonyl-L-ornithinamide. When an acid addition salt of an $N^2$-naphthalenesulfonyl-L-ornithinamide is used as the starting material, it is necessary to use a base in an amount sufficient to neutralize the acid addition salt.

The O-alkylisourea or S-alkylisothiourea is usually used in the equimolar amount.

Generally, the reaction of an $N^2$-naphthalenesulfonyl-L-ornithinamide or an acid addition salt thereof with an O-alkylisourea or an S-alkylisothiourea is conducted in a solvent.

The preferred solvents include: water, alcohols such as methanol, ethanol, propanol, etc.; ethers such as tetrahydrofuran, dioxane, tetrahydropyran, etc.; ketones such as acetone, methyl ethyl ketone, etc.; basic solvents such as dimethylacetamide, dimethylformamide, etc.; and mixtures of any two or more of them.

The reaction temperature varies with the $N^2$-naphthalene-sulfonyl-L-ornithinamide and base, and usually is between 0° C. and the boiling temperature of the solvent.

The reaction time varies with the $N^2$-naphthalenesulfonyl-L-ornithinamide, base, solvent and the employed reaction temperature, and usually is in the range of from 30 minutes to 30 hours.

After the reaction is completed, the solvent is distilled off and the excess base and the formed salt are removed by washing with water.

The $N^2$-naphthalenesulfonyl-L-argininamide is obtained by purifying the product by column chromatography with silica gel.

The thus obtained $N^2$-naphthalenesulfonyl-L-argininamide may be treated with ether and an acid such as hydrochloric acid, p-toluenesulfonic acid, etc. to isolate the acid addition salt of the $N^2$-naphthalenesulfonyl-L-argininamide.

$N^2$-naphthalenesulfonyl-L-arginine esters and amides of this invention having the formula (1) form acid addition salts with any of a variety of inorganic and organic acids. The product of the reactions described above can be isolated as the free base of as the acid addition salt. In addition, the product can be obtained as pharmaceutically acceptable acid addition salts by reacting one of the free bases with an acid, such as hydrochloric, hydrobromic, hydroiodic, nitric, sulfuric, phosphoric, acetic, citric, maleic, succinic, lactic, tartaric, gluconic, benzoic, methanesulfonic, ethanesulfonic, benzensulfonic, p-toluenesulfonic acid or the like.

As stated above, $N^2$-naphthalenesulfonyl-L-arginine esters and amides, and acid addition salts thereof of this invention are characterized by highly specific inhibitory activity in mammals against thrombin, and therefore these compounds are useful in the determination of thrombin in blood as diagnostic reagents, and/or for the medical control or prevention of thrombosis.

The antithrombotic activities of the $N^2$-naphthalenesulfonyl-L-arginine derivatives of this invention were compared with those of a known antithrombotic agent, [$N^2$-(p-tolylsulfonyl)-L-aginine methyl ester], by determining the fibrinogen coagulation time. The measurement of the fibrinogen coagulation time was conducted as follows:

An 0.8 ml aliquot of a fibrinogen solution, which had been prepared by dissolving 150 mg of bovine fibrinogen (Cohn fraction) supplied by Armour Inc. in 40 ml of a borate saline buffer (pH 7.4), was mixed with 0.1 ml of a borate saline buffer, pH 7.4, (control) or a sample solution in the same buffer, and 0.1 ml of a thrombin solution (5 units/ml) supplied by Mochida Pharmaceutical Co., Ltd. was added to the solutions in an ice bath. Immediately after mixing, the reaction mixture was transferred from the ice bath to a bath maintained at 25° C. Coagulation times were taken as the period between the time of transference to the 25° C. bath and the time of the first appearance of fibrin threads. In the cases where no drug samples were added, the coagulation time was 50 – 55 seconds.

The experimental results are summarized in Table 1. The term "concentration required to prolong the coagulation time by a factor of two" is the concentration of an active ingredient required to prolong the normal coagulation time 50 – 55 seconds to 100 – 110 seconds.

The concentration required to prolong the coagulation time by a factor of two for the known antithrombotic agent, $N^2$-(p-tolylsuofonyl)-L-arginine methyl ester, was 1100 μM.

The inhibitors are shown in Table 1 by indicating μ and R' in the general formula (11) and the added acid.

When a solution containing an $N^2$-naphthalenesulfonyl-L-arginine derivative of this invention was administered intravenously into animal bodies, the high antithrombotic activity in the circulating blood was maintained for from one to three hours. The halflife for decay of the antithrombotic compounds of this invention in circulating blood was shown to be approximately 30 minutes; the physiological conditions of the host animals (rat, rabbit, dog and chimpanzee) were well maintained. The experimental decrease of fibrinogen in animals caused by infusion of thrombin was satisfactorily controlled by simultaneous infusion of the compounds of this invention.

The acute toxicity values ($LD_{50}$) determined 24 hours after oral administration of substances of formula (1) in mice (male, 20 g) range from about 1,000 to 10,000 milligrams per kilogram of body weight. Representative $LD_{50}$ values, for example, for 4-[$N^2$-(5,6,7,8-tetrahydro-2-naphthalenesulfonyl)-L-arginyl]morpholine, 4-methyl-1-[$N^2$-(7-methoxy-2-naphthalenesulfonyl)-L-arginyl)]piperidien, and 4-methoxy-1-[$N^2$-(7-methoxy-2-naphthalenesulfonyl)-L-arginyl]piperidine are 3000, 3000, >3000 milligrams per kilogram, respectively.

The therapeutic agents of this invention may be administered to mammals, including humans, alone or in combination with pharmaceutically acceptable carriers, the proportion of which is determined by the solubility and chemical nature of the compound, chosen route of administration and standard pharmaceutical practice. For example, the compounds may be injected parenterally, that is, intramuscularly, intravenously or subcutaneously. For parenteral administration, the compounds may be used in the form of sterile solutions containing other solutes, for examples, sufficient saline or glucose to make the solution isotonic. The compounds may be administered orally in the form of tablets, capsules, or granules containing suitable excipients such as starch, lactose, white sugar and the like. The compounds may be administered sublingually in the form of troches or lozenges in which each active ingredient is mixed with sugar or corn syrups, flavoring agents and dyes, and then dehydrated sufficiently to make the mixture suitable for pressing into solid form. The compounds may be administered orally in the form of solutions which may contain coloring and flavoring agents.

Physicians will determine the dosage of the present therapeutic agents which will be most suitable, and dosages vary with the mode of administration and the particular compound chosen. In addition, the dosage will vary with the particular patient under treatment.

When the composition is administered orally, a larger quantity of the active agent will be required to produce the same effect as caused with a smaller quantity given parenterally. The therapeutic dosage is genrally 10 – 50 mg/kg of active ingredient parenterally, 10 – 500mg/kg orally per day.

Having generally described the invention, a more complete understanding of the synthetic processes for the compounds of this invention can be obtained by reference to the following specific examples, which are included for purposes of illustration only and are not intended to be limiting unless otherwise specified.

EXAMPLE 1

A suspension of 1.0 gram of $N^2$-(7-methoxy-2-naphthalenesulfonyl)-L-arginine in 15 ml of anhydrous methanol was saturated with dry hydrogen chloride for one hour. The reaction mixture was refluxed for an additonal one hour. After cooling, the reaction mixture was concentrated in vacuo. The residue was triturated with cold ethyl ether to give a crystalline product. After crystallization from methanolethyl ether, $N^2$-(7-methoxy-2-naphthalenesulfonyl)-L-arginine methyl ester hydrochloride was obtained in 95% yield; mp. 115 - 118° C.

Elemental analysis (as $C_{18}H_{24}O_4N_4S \cdot HCl$)

|  | C | H | N |
|---|---|---|---|
| Calculated: | 48.59 | 5.66 | 12.59 |
| Found: | 48.42 | 5.75 | 12.36 |

EXAMPLE 2

A mixture of 1.0 gram of $N^2$-(7-methoxy-2-naphthalenesulfonyl)-L-arginine, 1.0 gram of p-toluenesulfonic acid monohydrate in 5 ml of benzyl alcohol and 30 ml of benzene was refluxed for 5 hours, removing water by azeotropic distillation. After the solvent was removed by distillation, 100 ml of ethyl ether was added to the residue, giving a crystalline mass of $N^2$-(7-methoxy-2-naphthalenesulfonyl)-L-arginine benzyl ester p-toluenesulfonate in 94% yield; mp. 115 - 117° C.

Elemental analysis (as $C_{24}H_{28}O_5N_4S \cdot C_7H_8O_3S$)

|  | C | H | N |
|---|---|---|---|
| Calculated: | 51.70 | 5.55 | 9.65 |
| Found: | 51.59 | 5.39 | 9.71 |

EXAMPLE 3

In a mixture of 1.5 gram of L-arginine butyl ester dihydrochloride and 1.4 gram of $K_2CO_3$ in 10 ml of water was added dropwise a solution of 1.28 gram of 7-methoxy-2-naphthalenesulfonyl chloride in 10 ml of ethyl ether with vigorous stirring at 0 – 5° C. for a period of over 30 minutes. After the solution was kept at room temperature for 10 hours with stirring, a viscous deposit was separated and triturated with water and ethyl ether.

To a suspension of the resulting product in 20 ml of ethyl ether was added 2 grams of p-toluenesulfonic acid monohydrate with stirring to yield crystals of $N^2$-(7-methoxy-2-naphthalenesulfonyl)-L-arginine butyl ester p-toluene-sulfonate in 90% yield; mp. 75 – 77° C.

Elemental analysis (as $C_{21}H_{34}O_5N_4S \cdot C_7H_8O_3S$)

|  | C | H | N |
|---|---|---|---|
| Calculated: | 54.17 | 6.17 | 9.03 |
| Found: | 54.21 | 6.06 | 9.11 |

EXAMPLE 4

A 1.0 gram amount of $N^2$-(6-methoxy-2-naphthalenesulfonyl)-L-arginine methyl ester hydrochloride was dissolved in 2 ml of butylamine with vigorous agitation. After the resulting solution was allowed to stand at room temperature for 2 days, the butylamine was removed in vacuo and the residual syrup was washed well with 5 ml of water to obtain a powdery product. And then this powder was dissolved in minimum volume of acetic acid. To this solution ethyl ether was added to precipitate the viscous oily product. Reprecipitation from ethanol-ethyl ether gave $N^2$-(6-methoxy-2-naphthalenesulfonyl)-N-butyl-L-argininamide acetate in a powder form in 74% yield.

Elemental analysis (as $C_{21}H_{31}O_4N_5S \cdot C_2H_4O_2$)

|  | C | H | N |
|---|---|---|---|
| Calculated: | 54.20 | 6.92 | 13.74 |
| Found: | 54.11 | 6.88 | 13.57 |

EXAMPLE 5

To a mixture of 1.0 gram of 4-ethyl-1-(L-arginyl)-piperidine and 0.61 gram of $K_2CO_3$ in 10 ml of water was added dropwise a solution of 1.1 gram of 5-methoxy-1-naphthalenesulfonyl chloride in 30 ml of dioxane with vigorous stirring for a period of over 30 minutes while maintaining the temperature at 0° C. The reaction mixture was stirred for an additional 5 hours and the formed precipitate was removed by filtration. The solvent was evaporated, and to the residue was added 50 ml of $CHCl_3$. A small amount of the undissolved material was filtered and the solution was dried over anhydrous $Na_2SO_4$. To the stirred solution was added 20 ml of ether containing 0.5 gram of acetic acid to precipitate 4-ethyl-1-[$N^2$-(5-methoxy-1-naphthalenesulfonyl)-L-arginyl]piperidine acetate, which was purified by reprecipitation from a methanol-ethyl ether mixture in 72% yield.

Elemental analysis (as $C_{24}H_{35}O_4N_5S \cdot CH_3COOH$)

|  | C | H | N |
|---|---|---|---|
| Calculated: | 56.81 | 7.15 | 12.74 |
| Found: | 56.52 | 7.11 | 12.65 |

EXAMPLE 6

A suspension of 1.00 gram of $N^2$-(7-methoxy-2-naphthalenesulfonyl)-L-arginine and 5 ml of thionyl chloride was allowed to stand at room temperature for one hour with vigorous stirring. The addition of cold dry ethyl ether led to the precipitation of the hydrochloride of $N^2$-(7-methoxy-2-naphthalenesulfonyl)-L-argininyl chloride, which was washed several times with cold dry ethyl ether. The acid chloride was carefully added to 1.40 gram of 4-methylpiperidine with stirring and the mixture was cooled in an ice-salt bath. The mixture was then allowed to stand for one hour at room temperature. The excess 4-methylpiperidine was removed in vacuo to give an oil product. The oily product was extracted with 10 ml of chloroform and washed with 10 ml of water. The chloroform layer was evaporated to dryness. The residual material was triturated with a small amount of water to give crystalline 4-methyl-1-[$N^2$-(7-methoxy-2-naphthalenesulfonyl)-L-arginyl]-piperidine, which was collected and recrystallized from water-ethanol in 86% yield; mp. 225 – 9° C.(dec).

Elemental analysis (as $C_{23}H_{33}N_5O_4S$)

|  | C | H | N |
|---|---|---|---|
| Calculated: | 58.08 | 6.99 | 14.73 |
| Found: | 57.96 | 6.83 | 14.68 |

EXAMPLE 7

A 3.0 gram amount of 4-[$N^G$-nitro-$N^2$-(5-methoxy-1-naphthalenesulfonyl)-L- arginyl]morpholine was dissolved in 50 ml of ethanol and 5 ml of acetic acid. A 0.5 gram amount of palladium-black was added and the mixture was shaken in a stream of hydrogen for 100 hours at room temperature. After filtering off the catalyst, the filtrate was evaporated to give a viscous oily product. Reprecipitation from methanol-ethyl ether gave 4-[$N^2$-(5-methoxy-1-naphthalenesulfonyl)-L-arginyl]morpholine acetate in a powder form in 75% yield.

Elemental analysis (as $C_{21}H_{29}O_5N_5S \cdot CH_3COOH$)

|  | C | H | N |
|---|---|---|---|
| Calculated: | 52.86 | 6.17 | 13.40 |
| Found: | 52.57 | 6.11 | 13.20 |

EXAMPLE 8

A 1.0 gram amount of 4-ethyl-1-[$N^G$, $N^G$-dibenzyloxycarbonyl-$N^2$-(7-methoxy-2-naphthalenesulfonyl)-L-arginyl]-piperidine was dissolved in a mixture of 50 ml of ethanol and 5 ml of acetic acid. An 0.5 gram amount of palladium-black was added to the mixture, which was then shaken in a stream of hydrogen for 10 hours at room temperature. After filtering off the catalyst, the filtrate was evaporated to give a viscous oily product. Reprecipitation from ethanol-ethyl ether gave 4-ethyl-1[$N^2$-7methoxy-2-naphthalenesulfonyl)-L-arginyl]-piperidine acetate in a powder form in 76% yield.

Elemental analysis (as $C_{24}H_{35}O_4N_5S \cdot CH_3COOH$)

|  | C | H | N |
|---|---|---|---|
| Calculated: | 56.81 | 7.15 | 12.74 |
| Found: | 56.70 | 7.00 | 13.00 |

EXAMPLE 9

A 1.0 gram amount of 4-ethyl-1-[$N^G$-nitro-$N^2$-5-ethoxycarbonyloxy-1-naphthalenesulfonyl)-L-arginyl]-piperidine was dissolved in a mixture of 0.47 g of anisole and 10 ml of hydrogen fluoride, and the mixture was stirred for 30 minutes in an ice-bath. The hydrogen fluoride was evaporated in vacuo to afford an oily product, which was washed well with 100 ml of dry ethyl ether to remove the hydrogen fluoride. Reprecipitation from methanol-ethyl ether gave 4-ethyl-1-[$N^2$-(5-ethoxycarbonylcxy-1-naphthalenesulfonyl)-L-arginyl]-piperidine hydrofluoride in a powder form in 80% yield.

Elemental analysis (as $C_{26}H_{37}O_6N_5S \cdot HF$)

|  | C | H | N |
|---|---|---|---|
| Calculated: | 55.01 | 6.75 | 12.34 |
| Found: | 54.81 | 6.74 | 12.39 |

Table 1

$$\begin{array}{c} HN \\ \phantom{HN}\diagdown \\ \phantom{HNH_2N}C-N-(CH_2)_3-CHCOR \\ H_2N \diagup \phantom{XXXXX} | \\ \phantom{XXXXXXX} HN-SO_2-R' \end{array}$$

| No. | R | R' | Addition Moiety | Preparation process (Ex. No.) | Property or m.p. (°C) | Elemental Analysis Upper:Calculated Lower:Found C / H / N | Concentration required to prolong the coagulation time by a factor of the (μM) |
|---|---|---|---|---|---|---|---|
| 1 | −N⟨piperidine⟩−C₂H₅ | naphthyl-CH₃, OCH₃ | CH₃COOH | 5 | Powder | 56.81 7.15 12.74<br>56.52 7.11 12.65 | 0.3 |
| 2 | −N⟨piperidine⟩−CH₃ | " | " | 7 | Powder | 56.05 6.96 13.08<br>55.69 6.66 13.01 | 0.3 |
| 3 | −N⟨azepane⟩ | " | " | 7 | Powder | 56.05 6.96 13.08<br>56.31 6.87 13.02 | 0.7 |
| 4 | −N⟨morpholine⟩ | " | " | 7 | Powder | 52.86 6.17 13.40<br>52.57 6.11 13.20 | 2.0 |
| 5 | −N(CH₃)(n-C₄H₉) | " | — | 7 | Powder | 56.98 7.18 15.11<br>56.87 7.12 15.00 | |
| 6 | −NH(CH₂CH₂OCH₃) | " | CH₃COOH | 4 | Powder | 51.65 6.30 13.69<br>51.34 6.28 13.21 | 2.0 |
| 7 | −N(CH₃)(CH₂CH₂CO₂CH₃) | " | " | 7 | Powder | 52.06 6.37 12.65<br>52.04 6.29 12.95 | 65 |
| 8 | −N⟨piperidine⟩−C₂H₅ | naphthyl-OCH₃ | " | 7 | Powder | 56.81 7.15 12.74<br>56.49 7.40 12.34 | 0.2 |

Table 1-continued

| No. | R | R' | Addition Moiety | Preparation process (Ex. No.) | Property or m.p. (°C) | Elemental Analysis Upper:Calculated Lower:Found | | | Concentration required to prolong the coagulation time by a factor of the (μM) |
|---|---|---|---|---|---|---|---|---|---|
| | | | | | | C | H | N | |
| 9 | 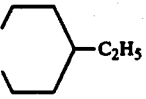 | 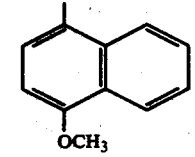 | " | 7 | Powder | 56.81<br>56.70 | 7.15<br>7.30 | 12.74<br>12.99 | 2.0 |
| 10 | 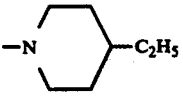 | 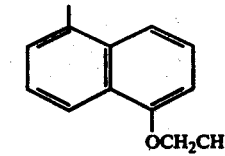 | " | 7 | Powder | 57.52<br>57.41 | 7.33<br>7.28 | 12.42<br>12.00 | 0.1 |
| 11 | " | 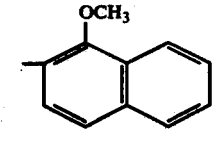 | " | 7 | Powder | 56.81<br>56.71 | 7.13<br>7.21 | 12.74<br>12.38 | 0.4 |
| 12 | 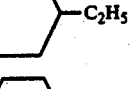 | 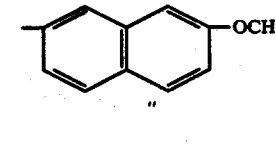 | CH₃COOH | 8 | Powder | 56.81<br>56.70 | 7.15<br>7.00 | 12.74<br>13.00 | 0.1 |
| 13 | 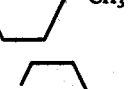 | " | — | 6 | 225–229 (dec) | 58.08<br>57.96 | 6.99<br>6.83 | 14.73<br>14.68 | 0.1 |
| 14 | 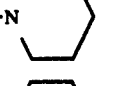 | " | CH₃COOH | 7 | Powder | 55.26<br>54.98 | 6.76<br>6.71 | 13.43<br>13.19 | 2.0 |
| 15 | 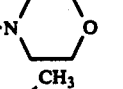 | " | — | 7 | Powder | 52.59<br>52.20 | 6.10<br>6.00 | 14.61<br>14.22 | 1.0 |
| 16 | 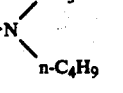 | " | CH₃COOH | 7 | Powder | 55.05<br>54.79 | 7.12<br>7.30 | 13.28<br>13.78 | 2.3 |
| 17 | 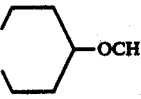 | " | " | 7 | Powder | 54.43<br>54.24 | 6.76<br>6.89 | 12.70<br>12.51 | 0.35 |
| 18 |  | 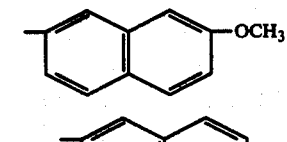 | CH₃COOH | 7 | Powder | 51.19<br>51.01 | 6.16<br>6.26 | 12.98<br>13.11 | 0.23 |
| 19 | 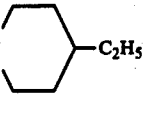 | 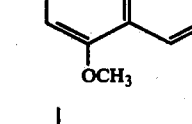 | " | 5 | Powder | 56.71<br>56.41 | 7.15<br>7.08 | 12.74<br>12.77 | 1.0 |
| 20 | " | 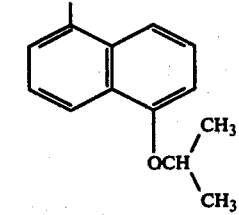 | " | 5 | Powder | 58.21<br>58.20 | 7.50<br>7.80 | 12.12<br>12.52 | 0.4 |

Table 1-continued

Structure header:

$$\begin{array}{c} HN\quad H \\ \phantom{HN}\diagdown\phantom{\quad}| \\ C-N-(CH_2)_3-CHCOR \\ / \phantom{C-N-(CH_2)_3-}| \\ H_2N \phantom{C-N-(CH_2)_3}HN-SO_2-R' \end{array}$$

| No. | R | R' | Addition Moiety | Preparation process (Ex. No.) | Property or m.p. (°C) | Elemental Analysis Upper:Calculated Lower:Found | | | Concentration required to prolong the coagulation time by a factor of the (μM) |
|---|---|---|---|---|---|---|---|---|---|
| | | | | | | C | H | N | |
| 21 | " | 5-methyl-1-(OCH₂CH₂CH₃)-naphthyl | " | 7 | Powder | 58.21<br>58.02 | 7.50<br>7.80 | 12.12<br>12.31 | 0.3 |
| 22 | −N(H)CH₂CH₂CH₂CH₃ | 6-methyl-2-OCH₃-naphthyl | " | 4 | Powder | 54.29<br>54.11 | 6.92<br>6.88 | 13.74<br>13.57 | |
| 23 | −N⟨piperidine-CO₂CH₃⟩ | " | " | 5 | Powder | 53.87<br>53.77 | 6.43<br>6.42 | 12.08<br>11.79 | |
| 24 | −N⟨azepane⟩ | 6-methyl-2-OCH₃-naphthyl | " | 7 | Powder | 57.52<br>57.59 | 7.33<br>7.28 | 12.42<br>12.38 | |
| 25 | −N⟨piperidine-COCH₃⟩ | " | " | 7 | Powder | 55.40<br>55.29 | 6.62<br>6.57 | 12.43<br>12.31 | |
| 26 | −N⟨isoindoline⟩ | " | " | 8 | Powder | 58.36<br>58.22 | 5.99<br>5.83 | 12.61<br>12.34 | |
| 27 | −N(H)CH₂-cyclohexyl | 5-methyl-1-OCH₃-naphthyl | " | 4 | Powder | 56.81<br>56.65 | 7.15<br>7.06 | 12.74<br>12.57 | |
| 28 | −N⟨piperidine-4-OCH₃⟩ | " | " | 7 | Powder | 54.43<br>54.38 | 6.76<br>6.59 | 12.70<br>13.00 | |
| 29 | −N⟨thiomorpholine⟩ | " | " | 7 | Powder | 51.19<br>51.01 | 6.16<br>6.22 | 12.98<br>12.77 | |
| 30 | −N⟨piperazine-N'-COCH₃⟩ | 5-methyl-1-OCH₃-naphthyl | CH₃COOH | 7 | Powder | 53.17<br>53.04 | 6.43<br>6.23 | 14.80<br>14.76 | |
| 31 | −N⟨piperazine-N'-CH₃⟩ | " | 2CH₃COOH | 7 | Powder | 52.33<br>51.87 | 6.76<br>6.71 | 14.09<br>14.00 | |
| 32 | −N⟨piperidine-4-(O)C₂H₅⟩ | 5-methyl-1-(OCOOC₂H₅)-naphthyl | HF | 9 | Powder | 55.01<br>54.81 | 6.75<br>6.71 | 12.34<br>12.39 | |
| 33 | −OCH₃ | 6-methyl-2-OCH₃-naphthyl | HCl | 1 | 113–118 | 48.59<br>48.42 | 5.66<br>5.75 | 12.59<br>12.36 | |
| 34 | −O-n-C₄H₉ | " | p-toluene- | 3 | 75–77 | 54.17 | 6.17 | 9.03 | 0.25 |

Table 1-continued

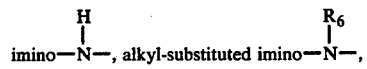

| No. | R | R' | Addition Moiety | Preparation process (Ex. No.) | Property or m.p. (°C) | Elemental Analysis Upper:Calculated Lower:Found C | H | N | Concentration required to prolong the coagulation time by a factor of the (μM) |
|---|---|---|---|---|---|---|---|---|---|
|  |  |  | sulfonic acid |  |  | 54.21 | 6.06 | 9.11 |  |
| 35 | —O-n-C$_6$H$_{13}$ | " | " | 2 | 155–156 | 55.36 55.28 | 6.50 6.48 | 8.61 8.51 | 0.8 |
| 36 | —OCH$_2$CH$_2$OCH$_3$ | " | " | 2 | 114–117 | 51.91 51.86 | 5.81 5.92 | 8.97 9.00 | 0.6 |
| 37 | —OCH$_2$CH$_2$CH$_2$Cl | " | " | 2 | 100–108 | 50.42 50.41 | 5.48 5.31 | 8.71 8.59 |  |
| 38 | —OCH$_2$—⟨phenyl⟩ | " | " | 2 | 115–117 | 51.70 51.59 | 5.55 5.39 | 9.63 9.71 | 0.35 |

What is claimed as new and intended to be covered by letters patent is:

1. An N$^2$-naphathalenesulfonyl-L-arginine amide having the formula:

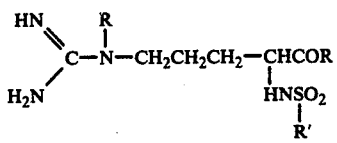

or the acid addition salt thereof with a pharmaceutically acceptable acid, wherein R is

wherein Z is a divalent group containing up to 20 carbon atoms which consists of more than one group selected from the class consisting of methylene —CH$_2$—, mono-substituted methylene

wherein R$_3$ is selected from the class consisting of alkyl, acyl, alkoxy and alkoxycarbonyl, respectively containing not more than 10 carbon atoms, and carbamoyl; and disubstituted methylene

wherein R$_4$ and R$_5$ are alkyl groups of not more than 10 carbon atoms, which further contains at least one member selected from the class consisting of oxy —O—, thio-S-, $$\overset{H}{\underset{|}{\text{imino—N—}}}, \text{ alkyl-substituted imino} \overset{R_6}{\underset{|}{\text{—N—}}},$$

wherein R$_6$ is an alkyl group of not more than 10 carbon atoms, acyl-substituted $$\overset{O=C-R_7}{\underset{|}{\text{imino—N—}}},$$

wherein R$_7$ is an alkyl group of not more than 10 carbon atoms; and R' is a member selected from the class consisting of 5,6,7,8-tetrahydro-1-naphthyl, 5,6,7,8-tetrahydro-2-naphthyl, 1-naphthyl, 2-naphthyl, 1-naphthyl substituted with one member selected from the class consisting of alkoxy and alkoxycarbonyloxy, respectively containing not more than 10 carbon atoms; and 2-naphthyl substituted with a member selected from the class consisting of alkoxy and alkoxycarbonyloxy; respectively containing no more than 10 carbon atoms.

2. The compound of claim 1, wherein R is

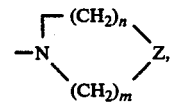

optionally substituted with at least one member selected from the class consisting of alkyl, acyl, alkoxy and alkoxycarbonyl, respectively containing not more than 10 carbon atoms, and carbamoyl, wherein Z is selected from the class consisting of oxy-O-, thio-S-,

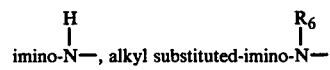

wherein R$_6$ is an alkyl group of not more than 10 carbon atoms, acyl-substituted imino

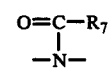

wherein R$_7$ is an alkyl group of not more than 10 carbon atoms, and carbonyl; m is an integer of 0, 1, 2 or 3; n is an integer of 0, 1 or 2; and m+n is an integer from 2 to 5.

* * * * *